United States Patent
Hebert et al.

(10) Patent No.: US 9,753,002 B2
(45) Date of Patent: Sep. 5, 2017

(54) HUMIDITY SENSOR WITH VOID WITHIN INTERCONNECT AND METHOD OF MANUFACTURING THE SAME

(71) Applicant: Magnachip Semiconductor, Ltd., Cheongju-si (KR)

(72) Inventors: Francois Hebert, San Mateo, CA (US); Ihl Hyun Cho, Daejeon-si (KR)

(73) Assignee: Magnachip Semiconductor, Ltd., Cheongju-si (KR)

( * ) Notice: Subject to any disclaimer, the term of this patent is extended or adjusted under 35 U.S.C. 154(b) by 260 days.

(21) Appl. No.: 14/606,435

(22) Filed: Jan. 27, 2015

(65) Prior Publication Data

US 2016/0025665 A1   Jan. 28, 2016

(30) Foreign Application Priority Data

Jul. 22, 2014  (KR) ........................ 10-2014-0092569

(51) Int. Cl.
*G01N 27/22* (2006.01)
*G01N 27/04* (2006.01)

(52) U.S. Cl.
CPC ......... *G01N 27/223* (2013.01); *G01N 27/048* (2013.01)

(58) Field of Classification Search
CPC .... G01N 27/048; G01N 27/223; G01N 27/22; G01N 27/04
See application file for complete search history.

(56) References Cited

U.S. PATENT DOCUMENTS

| | | |
|---|---|---|
| 6,690,569 B1 | 2/2004 | Mayer et al. |
| 7,554,134 B2 | 6/2009 | Cummins |
| 8,007,167 B2 | 8/2011 | Cummins |
| 8,357,958 B2 | 1/2013 | Cummins |
| 8,497,531 B2 | 7/2013 | Cummins |
| 8,507,954 B2 | 8/2013 | Cummins |
| 8,507,955 B2 | 8/2013 | Cummins |
| 8,633,047 B2 | 1/2014 | Hummel et al. |
| 8,648,395 B2 | 2/2014 | Cummins |
| 9,018,060 B2* | 4/2015 | Gryska ................ G01N 27/226 257/E21.351 |
| 2005/0218465 A1* | 10/2005 | Cummins ............ G01N 27/121 257/414 |
| 2006/0099328 A1* | 5/2006 | Waite ..................... B82Y 30/00 427/58 |

(Continued)

*Primary Examiner* — Jermele M Hollington
*Assistant Examiner* — Suresh K Rajaputra
(74) *Attorney, Agent, or Firm* — NSIP Law

(57) ABSTRACT

A humidity sensor and a method of manufacturing the same are provided where voids are formed within interconnects configured to facilitate the operation of the device and a humidity sensing material is deposited within the voids to detect the humidity. The accuracy with respect to the measurement of the humidity sensor is improved and manufacturing costs are lowered. The humidity sensor includes a substrate, a first interlayer insulating layer disposed on the substrate, first and second metal electrodes disposed adjacent to each other on the first interlayer insulating layer, an etch stop layer covering the first interlayer insulating layer and the first and second metal electrodes, a second interlayer insulating layer disposed on the first etch stop layer, voids formed within the second interlayer insulating layer, and a humidity sensing material deposited in the voids.

24 Claims, 7 Drawing Sheets

(56) References Cited

U.S. PATENT DOCUMENTS

| | | | |
|---|---|---|---|
| 2007/0273394 A1* | 11/2007 | Tanner | A01G 25/167 324/664 |
| 2013/0187670 A1* | 7/2013 | Dooley | G01N 27/223 324/686 |
| 2014/0159745 A1 | 6/2014 | Hummel et al. | |
| 2014/0291677 A1* | 10/2014 | Le Neel | H01L 25/0652 257/48 |

* cited by examiner

HUMIDITY SENSOR WITH VOID WITHIN INTERCONNECT AND METHOD OF MANUFACTURING THE SAME

CROSS-REFERENCE TO RELATED APPLICATION

This application claims the benefit under 35 USC §119(a) of Korean Patent Application No. 10-2014-0092569 filed on Jul. 22, 2014, in the Korean Intellectual Property Office, the entire disclosure of which is incorporated herein by reference for all purposes.

BACKGROUND

1. Field

The following description relates to a humidity sensor formed by voids within interconnects and a method of manufacturing the same. The accuracy with respect to the measurement of the humidity sensor is improved by depositing a humidity sensing material to detect humidity inside the voids. Accordingly, manufacturing costs can be reduced.

2. Description of Related Art

Recently, research for humidity sensor using a smart device has increased. Significant research is focused on Ubiquitous Sensor Network (USN) systems and Internet of Things (IoT) technologies to control the entire system based on the data provided from each sensor module. A humidity sensor that can be manufactured at low costs and has accuracy higher than the typical sensors is needed.

For the humidity sensor using a Chip Scale Packaging (CSP) or a Wafer Level Chip Scale Packaging (WLCSP), it is important to maintain a structure in which a top surface is planar to minimize stress which can lead to poor reliability. To this end, a passivation layer and a stress relief layer are needed. Such humidity sensors are typically based on capacitance sensor electrodes. A technique that maximizes an area of the electrode is needed in order to maximize the sensitivity.

However, the above configured structures and methods are few. Further, higher manufacturing costs are required to improve the sensitivity of the humidity than that of typical devices.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a humidity sensor including a substrate, a first interlayer insulating layer disposed on the substrate, first and second metal electrodes disposed adjacent to each other on the first interlayer insulating layer, an etch stop layer covering the first interlayer insulating layer and the first and second metal electrodes, a second interlayer insulating layer disposed on the first etch stop layer, voids formed within the second interlayer insulating layer, and a humidity sensing material deposited in the voids.

A portion of the first metal electrode and the second metal electrode may be surrounded by the humidity sensing material and another portion of the first metal electrode and the second metal electrode may be surround by the second interlayer insulating layer.

The portion of metal electrodes surrounded by the humidity sensing material may serve as a humidity sensing capacitor and another portion of the metal electrodes surrounded by the second interlayer insulating layer may serve as a reference capacitor.

The humidity sensor may be configured to detect humidity using a change in capacitance or resistance generated between the first and second metal electrodes.

The humidity sensor may further include a passivation layer disposed on the second interlayer insulating layer, and the humidity sensing material extends to an upper surface of the passivation layer.

The humidity sensor may further include a protective layer disposed on the humidity sensing material.

The humidity sensing material may be made up of polyimides and/or polymers

The etching stop layer may be any one or any combination of a silicon-rich oxide layer, a silicon-rich nitride layer, a silicon nitride layer, and a silicon oxynitride layer.

The first and second metal electrodes may comprise c-shaped member disposed in an interlocking manner.

Legs of the first and second c-shaped metal electrodes may be spaced apart.

The humidity sensor may further include a stress-relief layer disposed on the humidity sensing material and the passivation layer.

In another general aspect, there is provided a method of manufacturing a humidity sensor including disposing a first interlayer insulating layer on a substrate, disposing first and second metal electrodes adjacent to each other on the first interlayer insulating layer, disposing a first etch stop layer covering the first interlayer insulating layer, and the first and second metal electrodes, disposing a second interlayer insulating layer on the first etch stop layer, disposing a passivation layer on the second interlayer insulating layer, forming voids within the second interlayer insulating layer, and depositing the humidity sensing material in the voids.

A portion of the first and the second metal electrodes may be surrounded by the humidity sensing material and another portion of the first and the second metal electrodes may be surrounded by the second interlayer insulating layer.

The forming of the voids may include patterning the passivation layer and exposing the second interlayer insulating layer, etching the exposed second interlayer insulating layer, and exposing the first etch stop layer.

The method may further include disposing a protective layer on the humidity sensing material.

The method may further include depositing a second etching stop layer on surfaces of the voids.

An etch rate of the second interlayer insulating layer may be greater than an etch rate of the etch stop layer or the passivation layer.

In another general aspect, there is provided a humidity sensor including a first insulating layer disposed on a substrate, interconnect conductors disposed on the first interlayer insulating layer, an etch stop layer covering the first interlayer insulating layer and a portion of the interconnect conductors, a second insulating layer disposed on the first etch stop layer, voids formed within the second insulating layer, and a humidity sensing material deposited in the voids.

The interconnect conductors may include a top electrode, a bottom electrode, and a metal plug connecting the top electrode and the bottom electrode.

A cross-sectional area of the metal plug may be smaller than a cross-sectional area of the top electrode or the bottom electrode, and the metal plug may include a thin barrier metal.

At least one interconnect conductor may be surrounded by the humidity sensing material and at least one interconnect conductor may be surrounded by the second insulating layer.

Other features and aspects may be apparent from the following detailed description, the drawings, and the claims.

Figure 1:
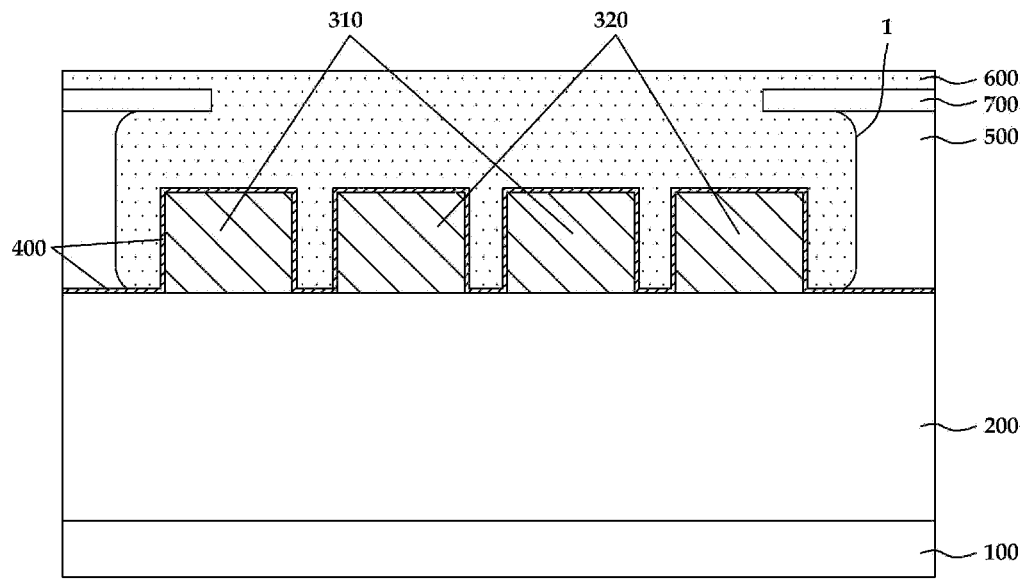
FIG. 1 is a diagram illustrating an example of a humidity sensor.

Throughout the drawings and the detailed description, unless otherwise described, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

It will be understood that when an element or layer is referred to as being "on" or "connected to" another element or layer, it can be directly on or connected to the other element or layer or through intervening elements or layers may be present. In contrast, when an element is referred to as being "directly on" or "directly connected to" another element or layer, there are no intervening elements or layers present. Like reference numerals refer to like elements throughout. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. These terms do not necessarily imply a specific order or arrangement of the elements, components, regions, layers and/or sections. Thus, a first element, component, region, layer or section discussed below could be termed a second element, component, region, layer or section without departing from the teachings description of the present invention.

Spatially relative terms, such as "lower," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a diagram illustrating an example of a humidity sensor. As illustrated in the example of FIG. 1, the humidity sensor includes a substrate 100, a first interlayer insulating layer 200 disposed on the substrate, two metal electrodes 310 and 320 disposed adjacent to each other on the first interlayer insulating layer 200, an etching stop layer 400 covering the first interlayer insulating layer 200 and the metal electrodes, a void 1 situated on the top of the etching stop layer 400, and a humidity sensing material 600 filing the void 1. The humidity sensing material 600 should be exposed to external environments (e.g., atmosphere) to sense the humidity. Thus, the humidity sensing material 600 is disposed at the upper surface of the semiconductor chip. Once moisture, gas or chemical material are absorbed by the humidity sensing material 600, dielectric constants of the humidity sensing material 600 positioned between two metal electrodes 310 and 320 are changed. According to such change, the capacitance of the humidity sensor is changed. It is possible to measure a change of the capacitance by using the two metal electrodes 310 and 320. In this way, it is possible to determine the amount of the moisture in the air. In the present examples, the humidity sensing material 600 is chosen to explain a sensing material to detect the humidity of the air. However, the present examples are not limited thereto and any materials that sense gas, chemical materials can be applied by conversion, without departing from the spirit and scope of the illustrative examples described.

By using such sensing material, the capacitance can be measured by applying positive (+) and negative (−) and alternating voltages to the first metal electrode 310 and the second metal electrode 320 when sensing the ambient environment data. However, this example is only intended to easily explain this application. In other words, it is possible that negative (−) voltage is applied to the first metal electrode 310 and that positive (+) voltage is applied to the second metal electrode 320.

Various substrates can be used with respect to the substrate 100, such as, for example, one or more of a P-type substrate, an N-type substrate, and a Silicon On Insulator (SOI) can be used with respect to the substrate 100. For example, P-type or N-type substrates are possibly applied with respect to the substrate 100. The substrate may also include materials such as, for example, Si, SiC, GaN, GaAs. In this example, an N-type WELL or a P-type WELL can be disposed to facilitate the operation of the device situated on the substrate.

A first interlayer insulating layer 200 is disposed on the substrate 100. One or more metal electrodes 310 and 320 are disposed on the first interlayer insulating layer 200 and adjacent to each other. The inside view of the first interlayer insulating layer 200 is not specifically illustrated. In various examples, the first interlayer insulating layer 200 may consist of one or more interlayer dielectrics (ILD, or other types of multi-level metal interconnection may be disposed inside the one or more ILD) insulated by one or more inter-metal dielectric (IMD) layers. One or more metal electrodes 310 and 320 may be a top metal of the metal interconnection (which is positioned at the top portion of the drawing). The humidity sensing material 600 is disposed between the two metal electrodes to detect the humidity of the environment.

The metal electrodes 310, 320, and an etching stop layer 400 are disposed on the first interlayer insulating layer 200. The etching stop layer 400 is disposed on the first interlayer insulating layer 200 and the metal electrodes 310 and 320. The etching stop layer 400 acts to prevent the metal electrodes 310 and 320 from damages due to the etch process of the second interlayer insulating layer 500. The etching stop layer 400 suppress reactions between the metal electrodes 310 and 320 and the moisture in the air. The etching stop layer 400 may comprise of materials, such as, for example, a silicon nitride layer, a silicon oxynitride layer, a compound of the two materials, a silicon-rich oxide, a silicon-rich nitride.

On the etching stop layer 400, a second interlayer insulating layer 500 is disposed, with a certain thickness. A part of the second interlayer insulating layer 500 is subject to a wet etching or a dry etching, and a void 1 is formed accordingly. The humidity sensing material 600 is formed within the void 1 by the subsequent process. The void 1 is also formed at a space between the metal electrodes 310 and 320. The humidity sensing material 600 is also disposed at a space between the metal electrodes 310 and 320.

In these examples, the void 1 is formed at a space between the etching stop layers 400. Thus, the humidity sensing material 600 is also formed between the etching stop layer 400.

A supplementary passivation layer 700 may be disposed on the second interlayer insulating layer 500. The passivation layer 700 may be composed of materials, such as, for example, silicon nitride. By disposing a passivation layer at the surface and periphery of the humidity sensor, the stabilization of the device characteristics can be achieved since detrimental environments which could impact the circuitry around the sensor, are blocked. Silicon nitride passivation layer 700 can have the benefit of reducing or blocking moisture penetration outside of the sensing region.

Further, the passivation layer 700 is able to act to remove stress that potentially occurs with respect to the semiconductor device such as the humidity sensor, by being relatively planar. Such passivation layer 700 may be various materials. For example, any technology that protects the entire structure of the semiconductor device from the external environment can be used with respect to the passivation layer 700.

The humidity sensor measures the humidity in the ambient air. To this end, the humidity sensing material 600 of the humidity sensor should be exposed to the ambient air. The example of FIG. 1 illustrates in relation to this the humidity sensing material 600 extends to the upper region of the passivation layer 700. Sensing material 600 outside of the sensor region can act as additional stress-relief when present over passivation layer 700.

Polyimides and Benzo-cyclo-Butene (BCB) and other polymers, may be used with respect to the humidity sensing material 600 of the present examples. However, the present examples are not limited to the discussed sensing material and other possible sensing materials may be used without departing from the spirit and scope of the illustrative examples described.

Figure 2A:
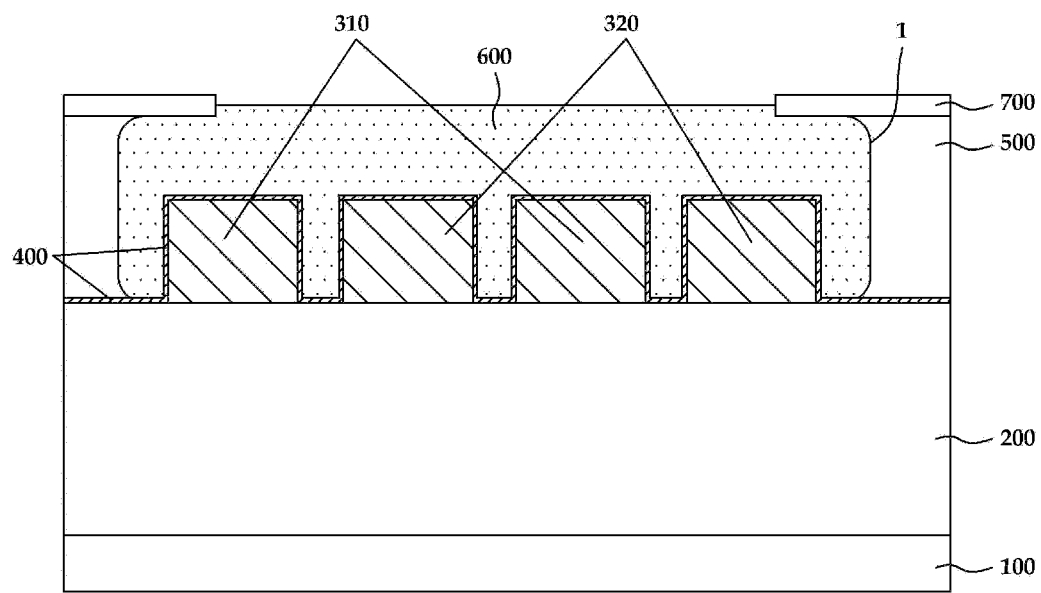
FIG. 2A is a diagram illustrating an example of a humidity sensor.

As illustrated in the example of FIG. 2A, the humidity sensing material 600 on the passivation layer 700 is absent. Such examples may be applied where a material that removes or reduces stress generated from the packaging process is deposited on the passivation layer 700.

Figure 2B:
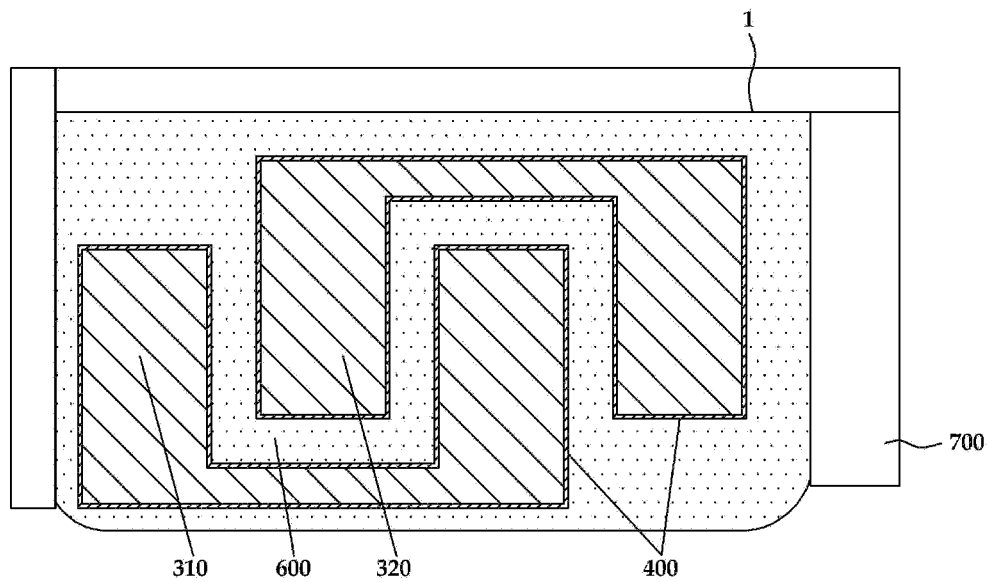
FIG. 2B is a diagram illustrating an example of a plan view of a humidity sensor.

FIG. 2B is a diagram illustrating an example of a plan view of a humidity sensor of the example of FIG. 2A. The example of FIG. 2B illustrates a top View of a humidity sensor structure capable of measuring a change in capacitance or resistance change as a result of moisture and humidity change, between the first metal electrode 310 and the second metal electrode 320. An etching stop layer 400 is disposed on the two metal electrodes 310 and 320. A passivation layer 700 surrounds the periphery of the structures. A humidity sensing material 600 disposed between the two metal electrodes 310 and 320 can be configured to contact sides of the two metal electrodes 310 and 320 as much as possible, so that the sensitivity can be improved. Even though the embodiment of FIG. 2B shows two pairs of electrodes, and other arrangements of electrodes are considered to be well within the scope of the present disclosure. For example, single finger electrodes could be used, or multiplefinger (more than 2) could also be used. Maximizing the number of parallel and adjacent fingers maximizes the sensitivity of the sensor.

Figure 3:
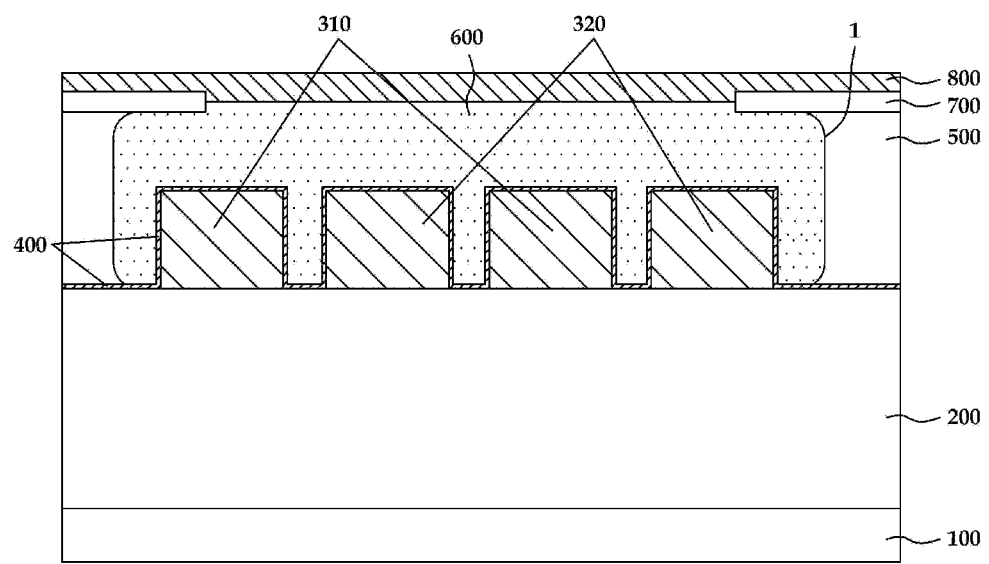
FIG. 3 is a diagram illustrating an example of a humidity sensor.

As illustrated in the example of FIG. 3, an additional stress-relief layer 800 may be disposed over the humidity sensing material 600 and the passivation layer 700. Different materials from the humidity sensing material 600 are applied as the stress-relief layer 800. According to the stress-relief layer 800, stress that potentially occurs with respect to the humidity sensor can be effectively removed or reduced. The stress-relief layer 800 acts to protect the humidity sensing material 600 and is referred as a protective layer.

Figure 4A:
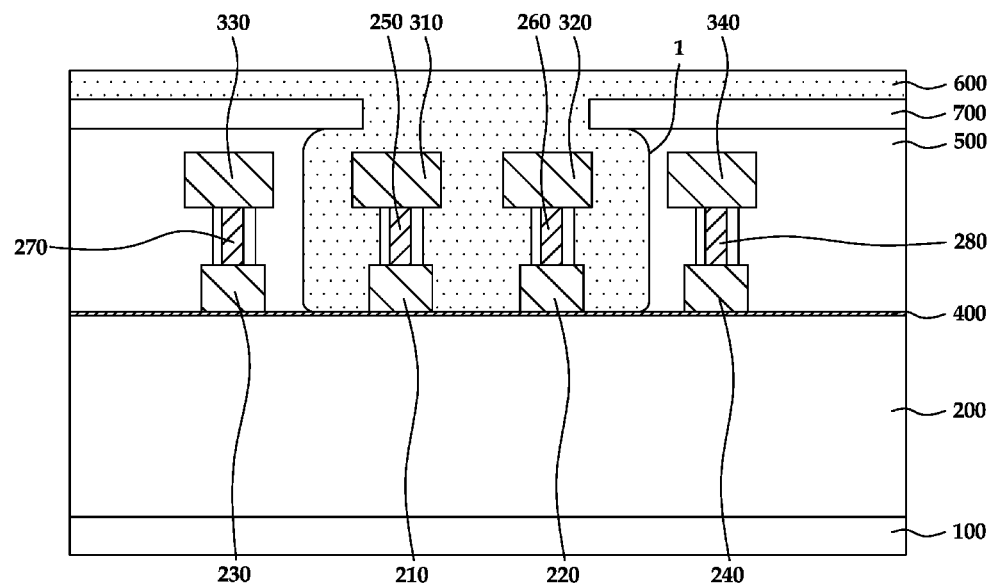
FIGS. 4A, 4B and 4C are diagrams illustrating examples of a humidity sensor.

As illustrated in the example of FIG. 4A, a plurality of interconnect conductors are provided. Each interconnect conductor may comprise bottom electrode 210, 220, 230 and 240, top electrode 310, 320, 330 and 340, and metal plug 250, 260, 270 and 280 formed between the bottom electrode and the top electrode. A metal plug 250, 260, 270 and 280 is a conductive structure used to fill and contact or via hole inside a dielectric. Metal plug 250-280 may consist of a thin barrier metal, such as, for example, Ti, TiN, TiW, and TiWN, deposited inside the contact or via that coats the sidewalls and bottom of the contacts or VIAS, followed by a Tungsten fill (W) and etchback. These metal plugs connect the bottom electrodes to the top electrodes and thereby maximize the sidewall area and height of the combined electrode to maximize sensitivity. Aluminum and/or copper conductor layers can also be stacked, with metal plugs in between. First interconnect conductor comprises bottom electrode 210, a metal plug 250 and top electrode 310. Similarly, second interconnect conductor comprises bottom electrode 220, a metal plug 260 and top electrode 320. As discussed above, the humidity sensing material 600 disposed between the first interconnect conductor and second interconnect conductor can contact the sides of the first interconnect conductor and the second interconnect conductor as much as possible to increase the sensitivity. Referring to the humidity sensor illustrated in the example of FIG. 4A, an area on which the humidity sensing material 600 comes in contact with the first interconnect conductor 210, 250 and 310 and the second interconnect conductor 220, 260, 320 increases in comparison to the example of FIG. 1. Thus, the sensitivity of the humidity sensor illustrated in the example illustrated in FIG. 4A increases in comparison with the sensing structure illustrated in the example illustrated in FIG. 1.

Both the first interconnect conductor 210, 250 and 310 and the second interconnect conductor 220, 260, 320 are surrounded by the humidity sensing material 600. Both the third interconnect conductor 230, 270 and 330, and the fourth interconnect conductor 240, 280 and 340 are surrounded by the second interlayer insulating layer 500. Both the first interconnect conductor 210, 250 and 310 and the second interconnect conductor 220, 260, 320 are sensitive to the moisture change because they are surrounded by the humidity sensing material. Thus, the first interconnect conductor 210, 250 and 310 and the second interconnect conductor 220, 260, 320 are used as a humidity sensing capacitor as that are surrounded by the humidity sensing material.

But both the third interconnect conductor 230, 270 and 330, and the fourth interconnect conductor 240, 280 and 340 are not sensitive to the humidity change as they are surrounded by the second interlayer insulating layer 500. The third interconnect conductor 230, 270 and 330, and the fourth interconnect conductor 240, 280 and 340 could be interconnect metal for other circuitry or devices. The third interconnect conductor 230, 270 and 330, and the fourth interconnect conductor 240, 280 and 340 can be used as lateral shielding. The third interconnect conductor 230, 270 and 330, and the fourth interconnect conductor 240, 280 and 340 can also be used as a reference capacitor. Here, all the first interconnect conductor 210, 250 and 310, the second interconnect conductor 220, 260, 320, the third interconnect conductor 230, 270 and 330, and the fourth interconnect conductor 240, 280 and 340 are coplanar with one another.

Figure 4B:
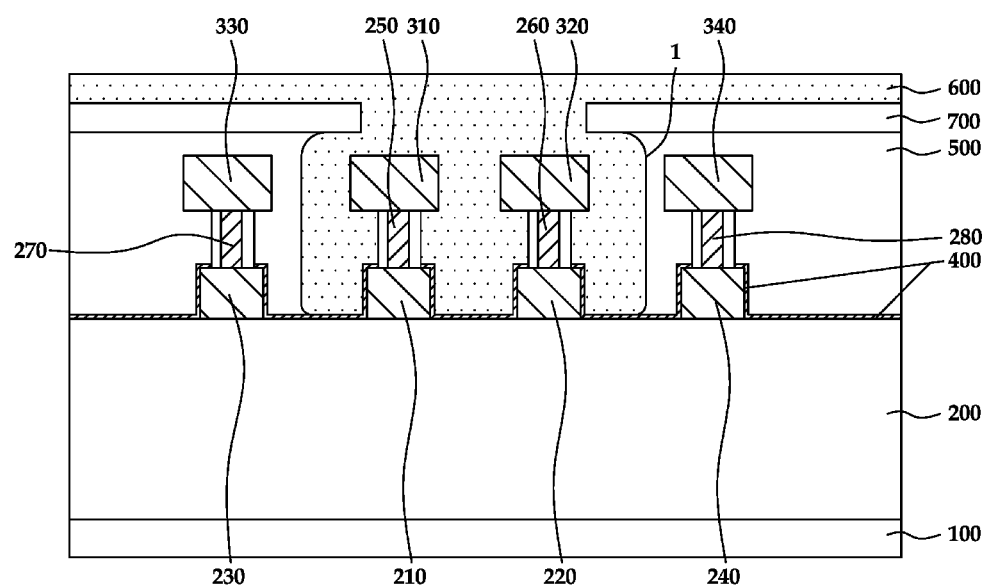

The example of FIG. 4A illustrates that a first etching stop layer 400 and a first interlayer insulating layer 200 are disposed under the first interconnect conductor 210, 250 and 310, and the second interconnect conductor 220, 260, 320. In another examples, as illustrated in the example of FIG. 4B, a first etching stop layer 400 may be disposed on top of the first layer of metal (bottom electrode) 210, 220, 230, and 240 which is part of the electrode structures of the first through fourth interconnect conductors. Such an structure prevents damage due to the moisture absorption to the first layer of metal (bottom electrode) 210 and 220.

Figure 4C:
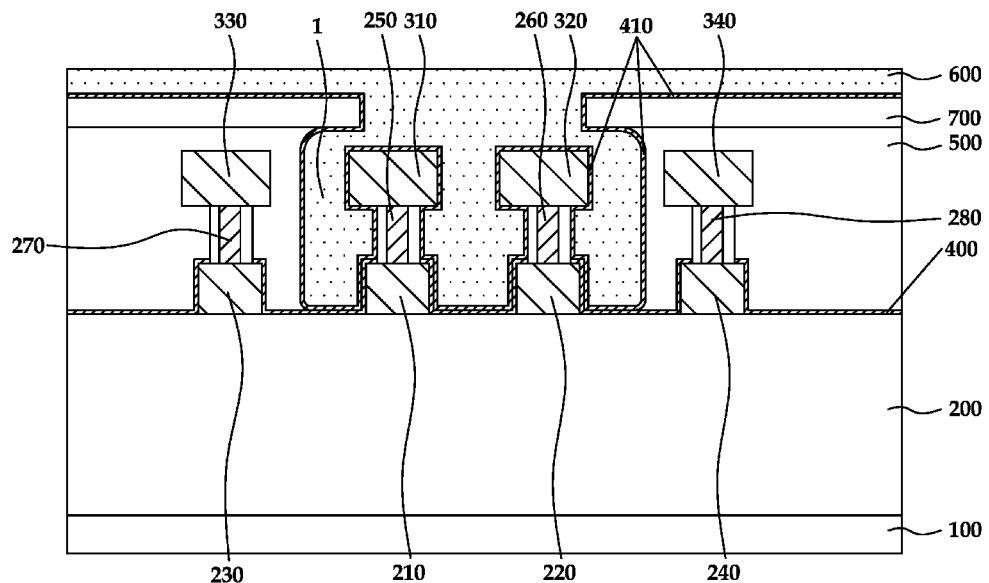

FIG. 4C is a diagram illustrating an example in which a second etching stop layer 410 is added. The second etching stop layer 410 is added after forming a void 1. The second etching stop layer 410 is disposed on surfaces of the sidewalls of the void, and the first interconnect conductor 210, 250 and 310, the second interconnect conductor 220, 260, 320, a passivation layer 700, and a first etching stop layer 400. The second etching stop layer 410 acts to improve the operation stability of the device by preventing the first interconnect conductor 210, 250 and 310, and the second interconnect conductor 220, 260, 320 from damage due to the moisture (humidity) absorbed on the humidity sensing material 600. In this example, an area on which the humidity sensing material 600 contacts the first interconnect conductor 210, 250 and 310, and the second interconnect conductor 220, 260, 320 increases, so that the sensitivity of the example of FIG. 4C increases greater than that of the sensing structure of FIG. 1. The first etching stop layer 400 and the second etching stop layer 410 act similarly and may be composed of the same material and may form two layers. The second etch-stop layer 410 can act as a passivation layer for the electrodes, so that they do not corrode when exposed to moisture and temperature. In the example of FIG. 4C, the first interconnect conductor 210, 250 and 310, and the second interconnect conductor 220, 260, 320 are also sensitive to the moisture change as they are surrounded by the humidity sensing material.

Figure 5:
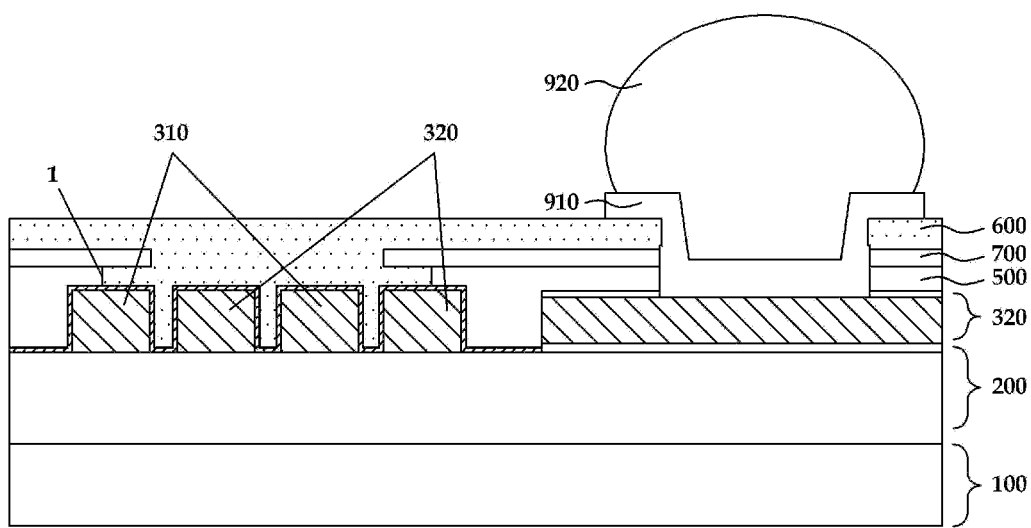
FIG. 5 is a diagram illustrating an example of a CSP(Chip Scare Package) to which the humidity sensor of this application is applied.

The humidity sensor described in the present examples may consist of a Chip Scale Package (CSP), as discussed in the example of FIG. 5. FIG. 5 is a diagram illustrating an example of a CSP(Chip Scare Package) that includes a humidity sensor. In the example of FIG. 5, a CSP (Chip Scare Package) is provided with a pad opening that is formed closer to the humidity sensor. With respect to the application of the typical CSP, a Under Bump Metallization (UBM) 910 is disposed on the structure of the humidity sensor so that a metal portion 320 and a solder ball 920 of the humidity sensor may be electrically connected. Subsequently, the solder ball 920 is situated on the UBM 910. During such process, high stress is generated since a great amount of power is applied downwardly to form the solder ball 920. To prevent the whole structure from damage such as, for example, cracking, during the formation of the solder ball 920, a material that can prevent stress is needed.

As discussed above, the humidity sensing material 600 of the present examples can reduce stress because polyimides used as a humidity sensing material 600 contribute to a stress relief. As illustrated in the example of FIG. 5, a UBM 910 and a solder ball 920 are situated on the humidity sensing material 600. In other examples, a structure, such as, for example, a copper pillar may be used instead of the solder ball.

Once a humidity sensing material 600 absorbs moisture, capacitance or resistance of the humidity sensing material 600 disposed between the metal electrodes are changed. The humidity sensor of the present example is able to measure humidity of the ambient environment by detecting the changed capacitance or resistance.

FIGS. 6A-6E discusses a method of manufacturing the humidity sensor described above.

Figure 6A:
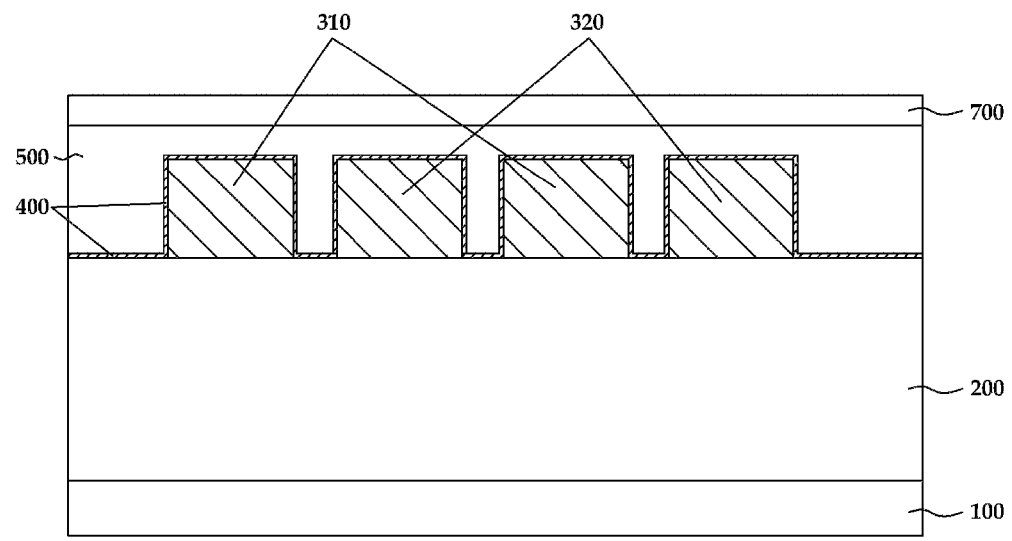
FIGS. 6A, 6B, 6C, 6D and 6E are diagrams illustrating examples of a method of manufacturing the same.

As illustrated in the example of FIG. 6A, a substrate 100 is prepared. Various substrates may be used with respect to the substrate 100 of the present example, such as, for example, one or more of a P-type wafer substrate, an N-type wafer substrate, and a silicon on insulator (SOI).

For example, a P-type wafer substrate or an N-type wafer substrate may be used with respect to the substrate 100. In such example, an N-type WELL or a P-type WELL may be applied on the substrate 100, to facilitate the operation of the device situated on the substrate. An SOI substrate may be used with respect to the substrate 100.

Various semiconductor devices, such as, for example, a passive device or an active device, may be disposed on the substrate 100. For example, many semiconductor devices such as a radio frequency (RF) switch device, an RF-SOI switch device, an RF-CMOS switch device, a Complementary Metal-Oxide Semiconductor (CMOS), an N-type Metal-Oxide Semiconductor (NMOS), a P-type Metal-Oxide Semiconductor (PMOS), a Laterally Diffused Metal-Oxide Semiconductor (LDMOS), a P-N diode, and a Schottky Diode may be used.

A device isolation layer (not shown) may be disposed for the isolation between devices formed on the substrate 100. A Shallow Trench Isolation (STI) or a local oxidation of silicon (LOCOS) oxide layer may be used with respect to the device isolation layer.

Such device isolation layer can be formed by various methods. For example, to form an STI, a trench may be formed on a substrate and the inside of the trench may be filled by an insulating layer. A LOCOS oxide layer may be formed by the LOCOS process forming a device isolation layer by selectively forming an oxide layer on a substrate.

A first interlayer insulating layer 200 is disposed on the substrate 100. One or more metal electrodes 310 and 320 are aligned adjacent to each other on the first interlayer insulating layer 200. The first interlayer insulating layer 200 may be one or more interlayer dielectrics (ILD), or other types of multi-level metal interconnection may be disposed inside the one or more ILD. One or more metal electrodes 310 and 320 may be a top metal of the metal interconnection, which is positioned at the top portion of the drawing. The humidity sensing material 600 is disposed between the two metal electrodes to detect the humidity of the environment.

An etching stop layer 400 is disposed on the first interlayer insulating layer 200 and the metal electrodes 310 and 320. The etching stop layer 400 prevents the metal electrodes 310 and 320 from damages due to the etch process of the second interlayer insulating layer 500. The etching stop layer 400 also suppress reactions of the metal electrodes 310 and 320 with the moisture in the air, such as corrosion. For the etching stop layer 400 may be composed of materials, such as, for example, a silicon nitride layer, a silicon oxynitride layer, a compound of the two materials, a silicon-rich oxide, or a silicon-rich nitride.

As shown in FIG. 6A, a second interlayer insulating layer 500 is disposed on the above structure. The same material can be used for the first interlayer insulating layer 200 and the second interlayer insulating layer 500. For example, a FSG (fluorinated or F-doped SiO2), a high density plasma (HDP) oxide layer, a tetraethylorthosilicate (TEOS) oxide layer, a plasma-enhanced chemical vapor deposition (PECVD) oxide layer may be used for the second interlayer insulating layer 500. A surface of the semiconductor device is planarized by the CMP(Chemical-Mechanical Planarization) process, and a passivation layer 700 is disposed on the second interlayer insulating layer 500. The passivation layer 700 is configured to protect the whole device and is achievable by the deposition process. To form voids, an etching process is needed. A material having an etching rate different from that of the second interlayer insulating layer 500 may be used. For example, a silicon nitride layer may be used with respect to the passivation layer 700.

Figure 6B:
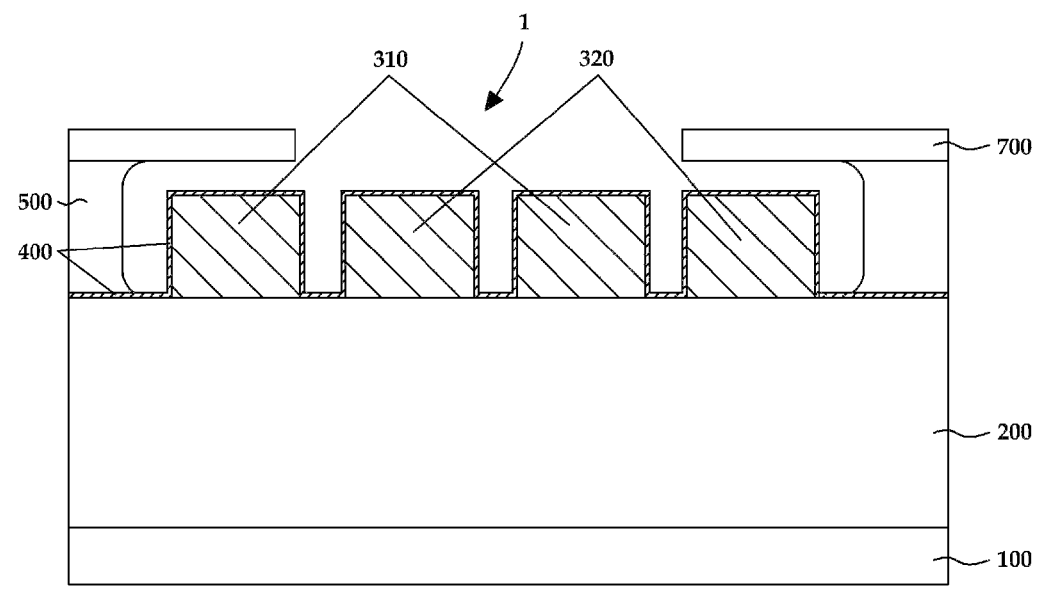

In the example of FIG. 6B, an etching process is performed for the patterning of the passivation layer 700 and the exposing of the second interlayer insulating layer 500. A mask process, an etch process and a process of forming an opening are possibly applied to form the void 1. The void 1 is formed within the second interlayer insulating layer by the isotropic etching process. The etch rate of material 500 is much faster than that of material 400 and 700 when exposed to the isotropic etch process. The region in which the void 1 is formed and the shape of the region may be varied according to the performance objectives of the humidity sensor, without departing from the spirit and scope of the illustrative examples described. For example, to improve the sensitivity of the humidity sensor, voids may be formed around the peripheries of the electrode (or the metal electrode), of which the operating performance is sensitive.

Both a dry etching and a wet etching may be used for the etching process to form the voids. In the present example, a wet etching is used. The wet etching may be easier to use rather than the dry etching for forming the voids because the wet etching removes an interlayer insulating layer. Wet etching includes, but is not limited to, HF-based etching. Dry etching includes plasma etching with SF6, CF4, NF3 type gasses alone, or in combination with other gasses (such as, for example, N2, O2, and H2).

The etching process may proceeds until the part of the etching stop layer 400 is exposed. Thus, the etching stop layer 400 may be a material strong to the etching (i.e., a material having a smaller etching rate than that of the second interlayer insulating layer 500). As described above, with respect to the etching stop layer 400, materials such as, for example, a silicon nitride layer, a silicon oxynitride layer, a compound of the two materials, a silicon-rich oxide, and a silicon-rich nitride may be used. The etching stop layer 400 and the passivation layer 700 may be composed of the same silicon nitride layer so that only the second interlayer insulating layer 500 may be etched during the process of the wet etching. The first and second metal electrodes 310 and 320 are protected by the etching stop layer.

Voids are formed in the second interlayer insulating layer 500 as the etching stop layer 400 is exposed by the etching process. The humidity sensing material 600 is used to fill the voids. The void 1 is formed between the passivation layer 700 and the etching stop layer 400 in the second interlayer insulating layer 500.

Figure 6C:
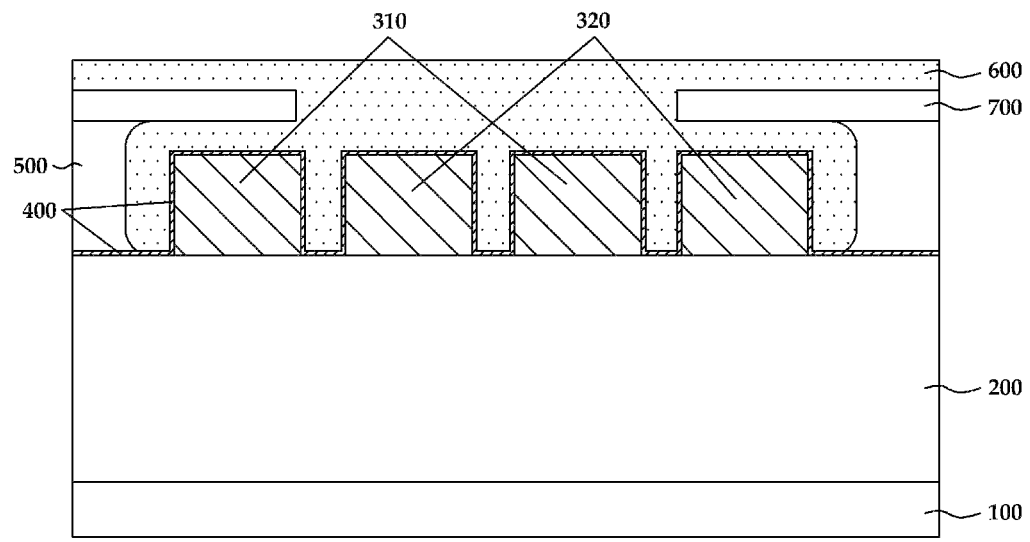

As illustrated in the example of FIG. 6C, the humidity sensing material 600 is deposited inside the void 1. Polyimides and Benzo-cyclo-Butene (BCB) and other polymer based materials, may be used for the humidity sensing material 600. However, these materials are only non-exhaustive examples, and any materials that changes characteristics when absorbing moisture (humidity) of the environment may be applied as the material 600 and are considered to be well within the scope of the present disclosure. The humidity sensing material 600 are deposited inside the void 1 by various methods, such as, for example, a spin-on method and a spray-on method. Any customary technical means that can deposit the material inside the void 1 can be applied for the technical operation. The humidity sensing material 600 may be deposited inside the void 1 and may extend on the partial region of the passivation layer 700. Such humidity sensing material 600 have the additional benefit of acting to reduce stress by being formed on the passivation layer 700. As illustrated in the example of FIG. 5, a CSP is provided.

Figure 6D:
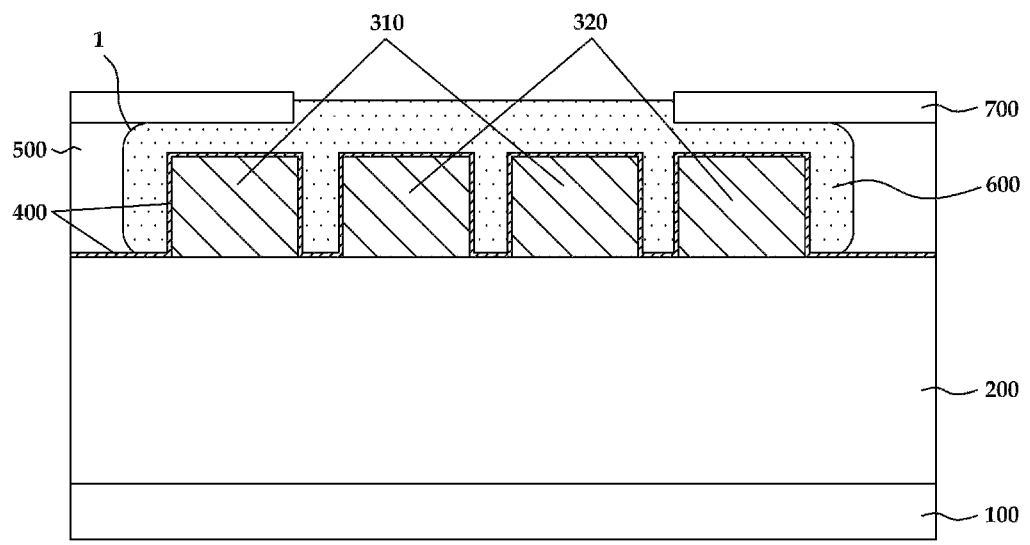

As illustrated in the example of FIG. 6D, it is possible that the humidity sensing material 600 disposed on the passivation layer 700 is removed by performing an etch-back process with respect to such material 600 provided in the example of FIG. 6C

Figure 6E:
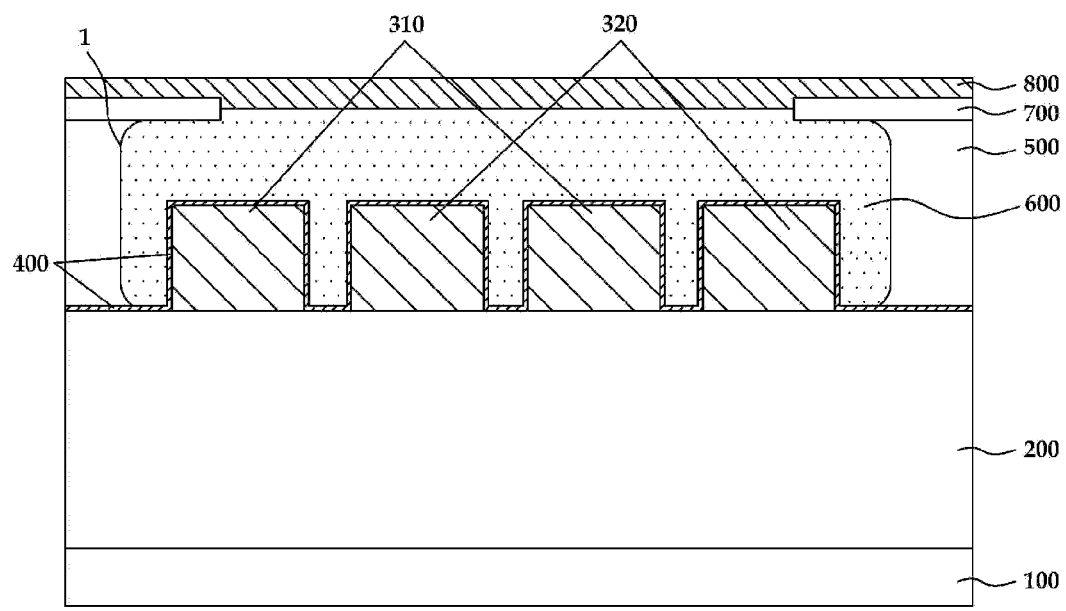

Further, as illustrated in the example of FIG. 6E, it is possible that the stress-relief layer 800 is additionally disposed on the structure illustrated in the example of FIG. 6D.

The structures illustrated in FIGS. 6A to 6E are only intended to provide some examples, but the present disclosures are not limited to the examples described. For example, as illustrated in the example of FIG. 5, a CSP is applied with respect to the example of FIG. 6C. Unlike in this example, a CSP is also applicable with respect to the example of FIG. 6E.

The humidity sensors described in the illustrative examples are achievable by various types of process. The accuracy in measuring can be improved and the humidity sensor having the sensitivity higher than that of the conventional device can be manufactured at lower costs.

According to a humidity sensor formed by voids with interconnects and a method of manufacturing the same described in the present disclosure, the measuring accuracy is improved by forming voids within interconnects configured to facilitate the operation of the humidity sensor and depositing humidity sensing materials inside the voids and reducing off-state capacitance. Further, manufacturing costs are lowered.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A humidity sensor comprising:
   a substrate;
   a first interlayer insulating layer disposed on the substrate;
   first and second metal electrodes disposed adjacent to each other and on a surface of the first interlayer insulating layer;
   an etch stop layer covering the first interlayer insulating layer and the first and second metal electrodes;
   a second interlayer insulating layer disposed on the etch stop layer;
   voids formed within the second interlayer insulating layer; and
   a humidity sensing material deposited in the voids.

2. The humidity sensor of claim 1, wherein a portion of the first metal electrode and the second metal electrode are surrounded by the humidity sensing material and another portion of the first metal electrode and the second metal electrode are surrounded by the second interlayer insulating layer.

3. The humidity sensor of claim 2, wherein the portion of metal electrodes surrounded by the humidity sensing material serves as a humidity sensing capacitor and another portion of the metal electrodes surrounded by the second interlayer insulating layer serves as a reference capacitor.

4. The humidity sensor of claim 1, wherein the humidity sensor is configured to detect humidity using a change in capacitance or resistance generated between the first and second metal electrodes.

5. The humidity sensor of claim 1, further comprising:
   a passivation layer disposed on the second interlayer insulating layer; and
   the humidity sensing material extends to an upper surface of the passivation layer.

6. The humidity sensor of claim 1, further comprising a protective layer disposed on the humidity sensing material.

7. The humidity sensor of claim 1, wherein the humidity sensing material comprises polyimides.

8. The humidity sensor of claim 1, wherein the etch stop layer comprises any one or any combination of a silicon-rich oxide layer, a silicon-rich nitride layer, a silicon nitride layer, and a silicon oxynitride layer.

9. The humidity sensor of claim 1, wherein the first and second metal electrodes comprise c-shaped member disposed in an interlocking manner.

10. The humidity sensor of claim 9, wherein legs of the first and second c-shaped metal electrodes are spaced apart.

11. The humidity sensor of claim 5, further comprising a stress-relief layer disposed on the humidity sensing material and the passivation layer.

12. A method of manufacturing a humidity sensor comprising:
    disposing a first interlayer insulating layer on a substrate;
    disposing first and second metal electrodes adjacent to each other and on a surface of the first interlayer insulating layer;
    disposing a first etch stop layer covering the first interlayer insulating layer, and the first and second metal electrodes;
    disposing a second interlayer insulating layer on the first etch stop layer;
    disposing a passivation layer on the second interlayer insulating layer;
    forming voids within the second interlayer insulating layer; and
    depositing the humidity sensing material in the voids.

13. The method of claim 12, wherein a portion of the first and the second metal electrodes are surrounded by the humidity sensing material and another portion of the first and the second metal electrodes are surrounded by the second interlayer insulating layer.

14. The method of claim 12, wherein the forming of the voids comprises:
    patterning the passivation layer and exposing the second interlayer insulating layer;
    etching the exposed second interlayer insulating layer; and
    exposing the first etch stop layer.

15. The method of claim 12, further comprising disposing a protective layer on the humidity sensing material.

16. The method of claim 12, further comprising depositing a second etch stop layer on surfaces of the voids.

17. The method of claim 14, wherein an etch rate of the second interlayer insulating layer is greater than an etch rate of the first etch stop layer or the passivation layer.

18. A humidity sensor comprising:
a first insulating layer disposed on a substrate;
interconnect conductors disposed on the first interlayer insulating layer;
an etch stop layer contacts the first interlayer insulating layer and a portion of the interconnect conductors;
a second insulating layer disposed on the etch stop layer;
voids formed within the second insulating layer; and
a humidity sensing material deposited in the voids.

19. The humidity sensor of claim 18, wherein the interconnect conductors comprise a top electrode, a bottom electrode, and a metal plug connecting the top electrode and the bottom electrode.

20. The humidity sensor of claim 19, wherein a cross-sectional area of the metal plug is smaller than a cross-sectional area of the top electrode or the bottom electrode, and the metal plug comprise a thin barrier metal.

21. The method of claim 18, wherein at least one interconnect conductor is surrounded by the humidity sensing material and at least one interconnect conductor is surrounded by the second insulating layer.

22. The humidity sensor of claim 1, wherein the first and second metal electrodes, the second interlayer insulating layer and the humidity sensing material are positioned adjacent to each other and in a same geometric plane that is parallel to a surface of the first interlayer insulating layer.

23. The humidity sensor of claim 1, wherein the etch stop layer is in contact with the first interlayer insulating layer, and in contact with the first and second metal electrodes.

24. The method of claim 12, wherein the first etch stop layer is in contact with the first interlayer insulating layer, and in contact with the first and second metal electrodes.

* * * * *